United States Patent
Colgate et al.

[11] Patent Number: 5,285,675
[45] Date of Patent: Feb. 15, 1994

[54] ACOUSTIC FLUID FLOW MONITORING

[75] Inventors: Samuel O. Colgate; Kenneth C. McGill, both of Gainesville, Fla.

[73] Assignee: University of Florida Research Foundation, Inc., Alachua, Fla.

[21] Appl. No.: 894,629

[22] Filed: Jun. 5, 1992

[51] Int. Cl.$^5$ ............................................. G01N 29/02
[52] U.S. Cl. ................... 73/23.2; 73/24.01; 73/24.05; 73/30.01; 73/31.04
[58] Field of Search ................. 73/61.41, 61.44, 61.46, 73/61.47, 61.49, 61.45, 23.2, 24.01, 30.01, 30.02, 30.03, 31.04, 24.05

[56] References Cited

U.S. PATENT DOCUMENTS

| | | | |
|---|---|---|---|
| 3,120,750 | 2/1964 | Root, III | 73/24.01 |
| 4,150,561 | 4/1979 | Zuponik | 73/24.01 |
| 4,280,183 | 7/1981 | Santi | 73/24.01 |
| 4,726,221 | 2/1988 | Tavlarides et al. | 73/61.45 |
| 5,060,514 | 10/1991 | Aylsworth | 73/24.01 |
| 5,076,094 | 12/1991 | Frye et al. | 73/61.49 |
| 5,115,670 | 5/1992 | Shen | 73/61.41 |
| 5,159,843 | 11/1992 | Shakkotoi et al. | 73/24.01 |

Primary Examiner—Hezron E. williams
Assistant Examiner—Michael Brock
Attorney, Agent, or Firm—Kerkam, Stowell, Kondracki & Clarke

[57] ABSTRACT

A method of measuring the flow and composition of a fluid or mixture of fluids through a system by determining the temperature, pressure and speed of sound in the fluid or mixture of fluids in the system and calculating the flow, molar density and average molecular weight of the fluid from the equation:

$$c^2 = \frac{\tau}{M} \left( \frac{\delta P}{\delta \rho} \right)_T,$$

$$\nabla^2 \phi = \frac{1}{c^2} \frac{\delta^2 \phi}{\delta t^2}$$

wherein:

$$\tau = \frac{c_P}{c_\rho}$$

c = speed of sound
P = pressure of the fluid
T = temperature of the fluid
$\rho$ = molecular density of the fluid
M = average molecular weight of the fluid
$\phi$ = velocity potential
t = time.

4 Claims, 5 Drawing Sheets

Sonic Domain

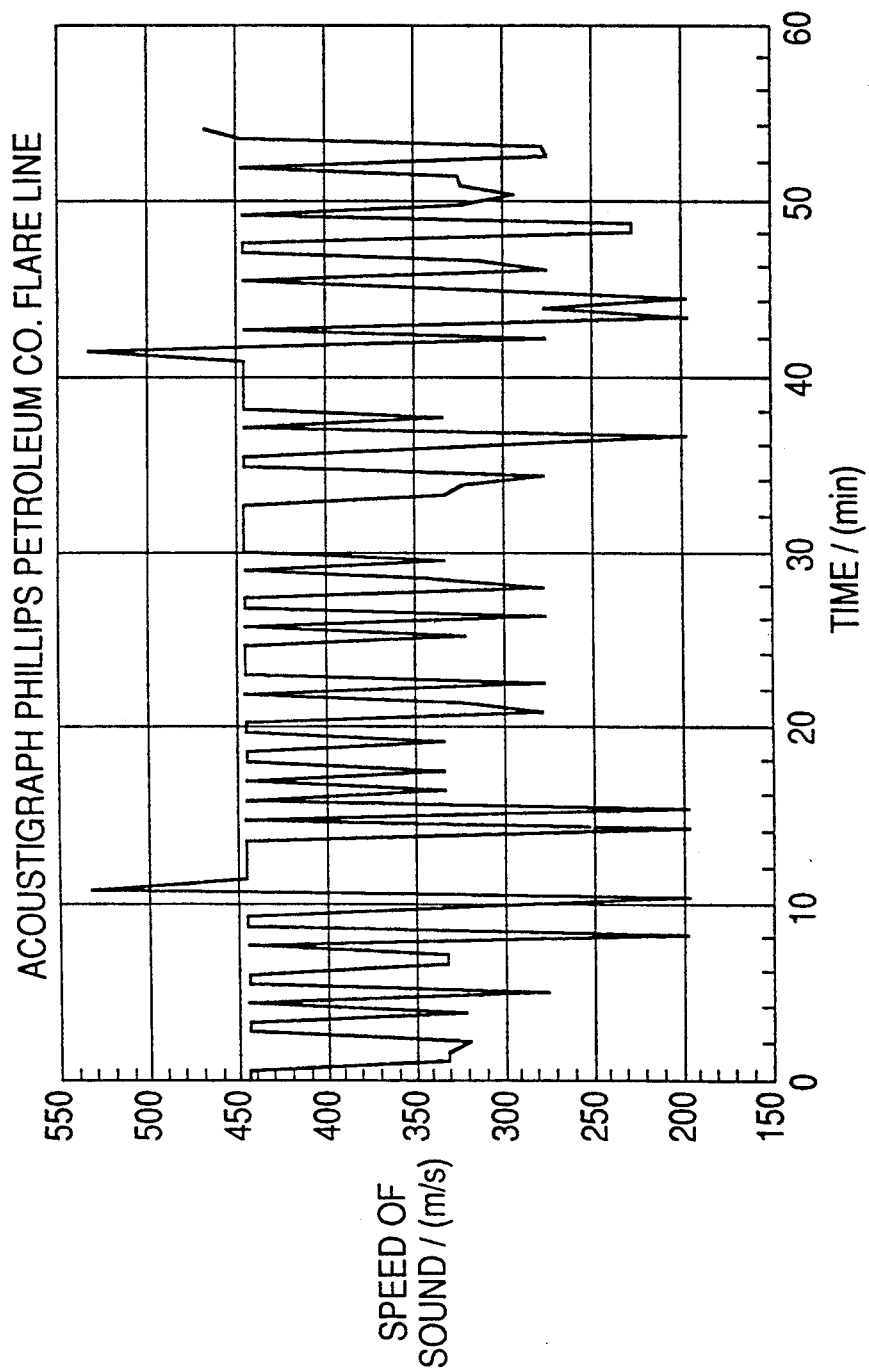

ACOUSTIC FLUID FLOW MONITORING

BACKGROUND OF THE INVENTION

1. Field of the Invention

The present invention relates to a system and method for measuring fluid flow and other fluid characteristics in a pipe or other structure.

2. The Prior Art

Many and diverse systems are currently employed in the industry to measure the flow rate of fluids in pipes and other structures and to determine other characteristics of the flowing fluid such as composition, density, molecular weight, etc.

To date, it has been necessary to employ multiple devices to achieve these ends. Presently employed flow measurement techniques include ultrasonic doppler flow meters, magnetic flow meters, etc. None of these devices is passive, however, and all are difficult to install, calibrate and utilize.

Devices employed to determine other characteristics of the flowing fluids require sampling windows or probes which affect the flow of fluid in the line and interject the danger of possible contamination of the fluid during the sampling procedure. Moreover, these invasive devices also require a great deal of maintenance, supervision and calibration.

It is an object of the present invention to provide a passive, non-invasive method and system for monitoring the flow of fluids and other characteristics of the fluid which are not subject to the above-noted and other disadvantages.

SUMMARY OF THE INVENTION

These and other objects are realized by the present invention which provides a method of measuring the flow and composition of a fluid or mixture of fluids through a system by determining the temperature, pressure and speed of sound in the fluid or mixture of fluids in the system and calculating the flow, molar density and average molecular weight of the fluid from the equation:

$$c^2 = \frac{\tau}{M} \left( \frac{\delta P}{\delta \rho} \right)_T$$

wherein:

$$\tau = \frac{c_P}{c_\rho}$$

$C_P$ = isobaric heat capacity
$C_\rho$ = isochoric heat capacity
$c$ = speed of sound
$P$ = pressure of the fluid
$T$ = temperature of the fluid
$\rho$ = molecular density of the fluid
$M$ = average molecular weight of the fluid;

a) the molar density of the fluid being determined from the equation of state (EOS) over a small temperature range T-T' and composition range:

$$\left( \frac{\delta P}{\delta \rho} \right)_T = f(P, c)_T$$

wherein:
f = any EOS
T' = average temperature; and b) the average molecular weight of the fluid being determined from the equation:

$$\frac{c^2}{f(P, c)_T} = \frac{\tau}{M}$$

wherein:
f = any EOS.

BRIEF DESCRIPTION OF THE DRAWINGS

FIGS. 1-5 depict graphical results of the method of the invention as described in the example hereinbelow.

DETAILED DESCRIPTION OF THE INVENTION

Figure 1:
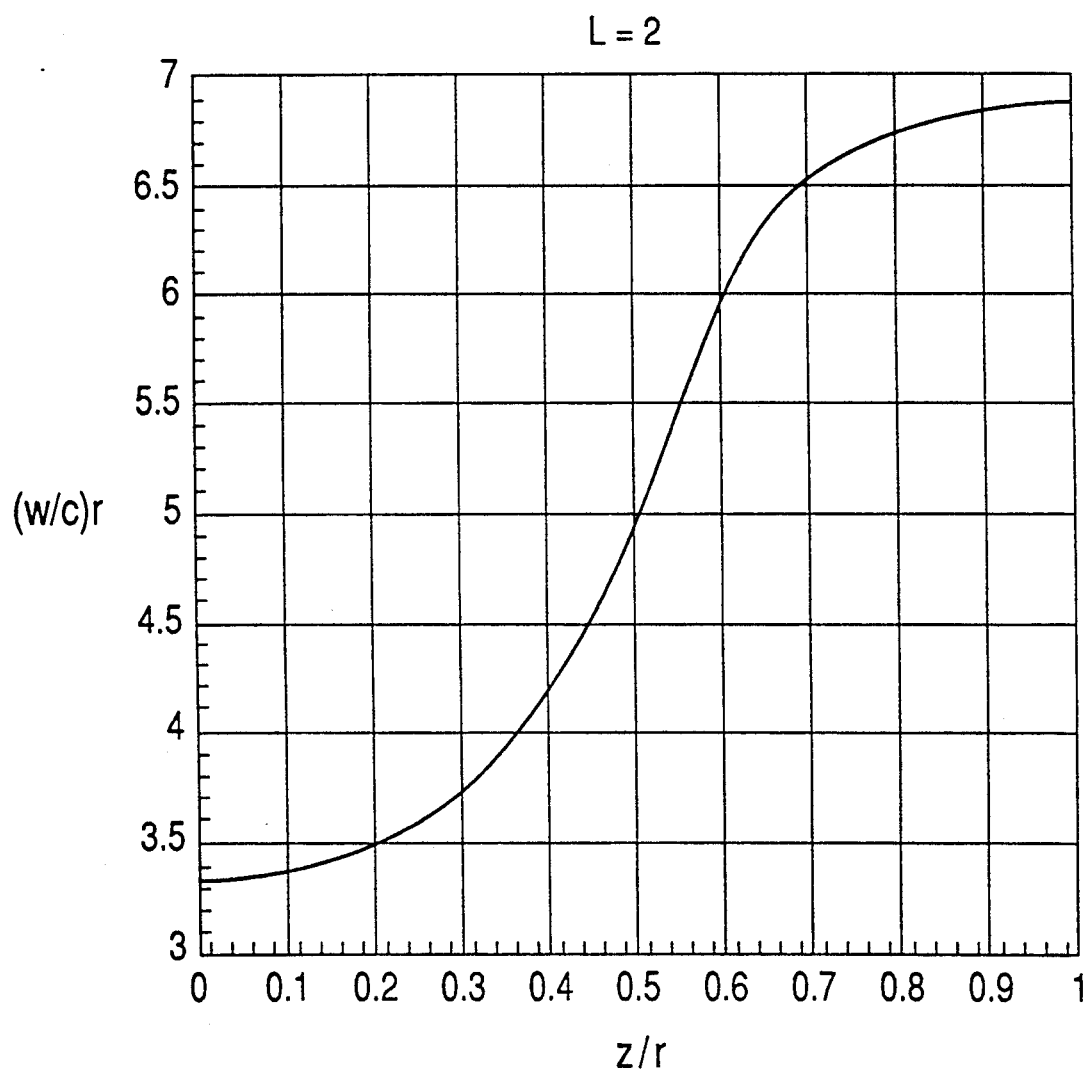

The purpose of the system of the invention is to measure the flow of a fluid or a mixture of fluids through any structure (pipeline, chimney or turbine). Devices to measure flow through pipelines have already been developed, but they monitor flow only. The proposed system will not only measure flow, but also composition (average molecular weight, density, ratio of heat capacities and phase). It is a passive system that uses the sound already in the structure to identify these properties. The method used in the industry at the moment is to sample the flow at regular intervals and then use controlled laboratory analytical means to find the composition of the material. Laboratory analytical devices to date require extremely controlled environments in order to be effective. Also any on-line real time chromatographic device would require some kind of sampling window that would need special installation and maintenance. An automatic sample device would be perturbed due to the method in which it samples and would require a great deal of maintenance. The acoustic flow monitor (AFM) system of the present invention is a passive and easy-to-employ system that requires almost no maintenance. It works in real time so that the results can be used interactively to adjust the composition within the structure.

Different compositions of fluids propagate sound at different speeds:

$$c^2 = \frac{\tau}{M} \left( \frac{\delta P}{\delta \rho} \right)_T$$

wherein:

$$\tau = \frac{c_P}{c_\rho}$$

$C_P$ = isobaric heat capacity
$C_\rho$ = isochoric heat capacity
$c$ = speed of sound
$P$ = pressure of the fluid
$T$ = temperature of the fluid
$\rho$ = molecular density of the fluid
$M$ = average molecular weight of the fluid.

The above relation shows how the speed varies with state variables (P, rho, T) and that $$c^2 \alpha \frac{\tau}{M}.$$

Since speed is also a state variable, an equation of state for these variables can be developed that is very accurate over a small temperature range. Once this equation is found, then the partial derivative with respect to rho can also be determined:

$$\left(\frac{\delta P}{\delta \rho}\right)_T = f(P, c)_T$$

$$\frac{c^2}{f(P, c)_T} = \frac{\tau}{M}.$$

The ratio of $\tau$ over the average molecular weight is extremely dependent on the composition of the mixture. From the equation of state, the molar density can also be determined.

An example of an equation of state is as follows:

$$P = \rho R T (B_i + B_2 \rho)$$

wherein:
$\rho$ = molar density
R = universal gas constant
T = absolute temperature
$B_i$ = ith virial coefficient.

An example of its relation to the speed of sound is:

$$P = \frac{1}{4B_2}\left(\frac{Mc^2}{\tau RT} - B_i\right)^2 + \frac{B_i}{2B_2}\left(\frac{Mc^2}{\tau RT} - B_i\right)$$

c = speed of sound $$\tau = \frac{c_p}{c_\rho}$$

M = molecular weight.

Those skilled in the art will understand that this equation is valid over a given temperature range T' depending on which equation of state is used. Since T', P and c are measured, one can now calculate $$\frac{\tau}{M}.$$

For any geometry, the relationship of resonance in a cavity is given by $$f(i) = c \, G_i(x, y, z)$$

G = geometric function.

Hence, the spectrum of resonant frequencies is like a fingerprint of the speed of sound in the cavity. By placing a transducer (microphone) on the structure, a digitized waveform which contains all frequencies of sound is obtained. The wave is in time-domain form at this point. Transforming this wave to the frequency domain by use of a Fast Fourier Transform (FFT) yields a spectrum that reveals all of these same frequencies. Only certain frequencies will follow the above relation; these are the frequencies of the material inside the structure. Through a two-dimensional sonic transform, the speed of sound is found directly. The two-dimensional transform yields another component Z/1 known as the length of the resonance cavity factor. This length of resonance cavity factor is inversely proportional to the volume flow within the cavity. The actual value is found from the reduced variable x in equation (13) below.

There are active devices now available that measure flow using acoustic techniques based exclusively on the doppler effect, but these devices reveal no indication of the speed of sound and are costly to install. The novelty of the AFM system of the invention is its ease of application. The system is applicable to any structure simply by attaching a thermometer, pressure gauge and microphone. Other benefits derived from the system are that the elements needed are durable and require little maintenance. The composition of the cavity as far as the sound is detected is revealed; it works in very harsh environments and it can be used interactively for process control.

Recently, there has been a significant discovery of multiple sonic speeds ("Fast Sound," Campa and Cohen, Phys. Rev. 1989) in mixtures of gases. The AFM system detects all resonant speeds within a mixture. This system would be a very valuable research tool for work in this area. Also, application of this effect leads directly to information about the composition of the gas mixture; in this case, no equation of state is needed. Also, the accuracy of the system is enhanced by this effect, as well as its speed of operation.

In addition to all of the above-mentioned benefits, thermodynamic properties of the mixtures are determined interactively with the AFM system, since the AFM system detects three state variables simultaneously, thermodynamic properties may be calculated without an equation of state. It is like a thermodynamic metering device that reveals enormous amounts of information about the material within the conduit.

This technique is concerned with monitoring the speed of sound in the turbulent flow of fluid streams confined to pipelines and similar structures using acoustics. The underlying principle is that naturally occurring vibrations stimulated in the flowing system are dependent on the system structure and dynamics.

The principal property under immediate investigation is sonic speed. Other characteristics under consideration include volume flow and composition.

The theory of the technique of the invention is that in a high flow system, a large amount of information is being produced already as the gas rumbles and shakes its way down the pipe. Much of this information can be obtained by simply listening to the pipe with a microphone. Understanding the signals requires suitable theoretical models. In general, the free vibrations of a contained fluid satisfy the wave equation:

$$\nabla^2 \phi = \frac{1}{c^2} \frac{\delta^2 \phi}{\delta t^2} \quad (1)$$

where $\phi$ is a velocity potential and c is the speed of sound in the medium. By introducing a harmonic dependence $$\phi = \phi_o e^{i\omega t} \quad (2)$$

it is evident that $\phi_o$ satisfies a scaler Helmholtz equation $$\nabla^2 \times \phi_o + \frac{\omega}{c}^2 \phi_o = 0. \quad (3)$$

In spherical coordinates, the solution for the velocity potential $\phi_o$ is $$\phi_o = j_1\left(\frac{\omega}{c} r\right) P_1^m(\cos\theta)(A\cos(m\phi) + B\sin(m\phi)) \quad (4)$$

where $j_1$ is a spherical bessel function and $P_1^m$ is the associated Legendre polynomial. The velocity (v) of the fluid is $$v = -\phi_o. \quad (5)$$

For a spherical cavity, the velocity must be zero at the cavity walls; hence, the boundary condition is $$\frac{d}{dr} j_1\left(\frac{\omega}{c} r\right)_{r=wall} = 0. \quad (6)$$

The boundary conditions for a pipeline are different. They are best described in cylindrical coordinates where the z-axis runs parallel to the center of the pipe. In this case, equation (4) becomes $$\phi_o = j_1\left(\frac{\omega}{c} \sqrt{\rho^2 + z^2}\right) P_1^m\left(\frac{z}{\sqrt{\rho^2 + z^2}}\right)(A\cos(m\phi) + B\sin(m\phi)). \quad (7)$$

For detection of free vibration at the walls of the pipe, the boundary condition is that the velocity must be zero at the wall of the pipe $$\int \bar{v} \cdot d\bar{a} = 0, \; d\bar{a} = \rho d\phi dz \hat{\rho}. \quad (8)$$

The flow along the pipe is given by $$\text{flow} = \int \bar{v} \cdot d\bar{a}, \; d\bar{a} = \rho d\rho d\phi \hat{z}. \quad (9)$$

The boundary condition at the wall over some arbitrary length L is $$\rho \int_{-L}^{L} \frac{\partial}{\partial \rho} j_1\left(\frac{\omega}{c} \sqrt{\rho^2 + z^2}\right) P_l^m\left(\frac{z}{\sqrt{\rho^2 + z^2}}\right) dz \int_0^{2\pi} (A\sin(m\phi) + B\cos(m\phi)) d\phi = 0. \quad (10)$$

Any integration over $\chi$ will be zero except for m 0; hence, only the m=0 modes are observed. The resulting expression is then $$\int_0^L \frac{\partial}{\partial \rho}\left(j_1\left(\frac{\omega}{c} \sqrt{\rho^2 + z^2}\right) P_1\left(\frac{z}{\sqrt{\rho^2 + z^2}}\right)\right) dz = 0. \quad (11)$$

Since the integration over z is arbitrary but finite, the only way in general for this integral to be zero is if the integrand is zero, or $$\frac{\omega}{c} \sqrt{\rho^2 + z^2} \frac{j_1'\left(\frac{\omega}{c}\sqrt{\rho^2+z^2}\right)}{j_1\left(\frac{\omega}{c}\sqrt{\rho^2+z^2}\right)} - \frac{z}{\sqrt{\rho^2+z^2}} \frac{P_1'\left(\frac{z}{\sqrt{\rho^2+z^2}}\right)}{P_1\left(\frac{z}{\sqrt{\rho^2+z^2}}\right)} = 0. \quad (12)$$

Because the radius rho of the pipe is arbitrary, solutions are calculated in reduced coordinates x and y that are defined as $$x = \frac{\omega}{c} \sqrt{\rho^2 + z^2}, \; y = \frac{z}{\sqrt{\rho^2 + z^2}}. \quad (13)$$

Then equation (12) can be represented much more simply as $$x \frac{j_1'(X)}{j_1(X)} = y \frac{P_1'(y)}{P_1(y)}. \quad (14)$$

The resulting solution yields a basis set of frequencies for a given value of x and y. Current research involves solving this equation numerically to obtain values of x correlated to y. Then after acquiring an experimental set of time domain signals of a known gas flowing through a pipe, an FFT generates the associated frequency domain. A further transformation generates the two-dimensional domain of c and z. Once in this domain, the speed of sound of the gas in the pipe can be deduced by inspection or by sorting amplitudes for the highest weighted value.

The two-dimensional sonic transform algorithm is set forth below in terms of the reduced variables x and y from equation (13). Once these values are obtained from the solution to equation (14), the geometric factor G can be represented in these terms. It should be noted that xyz in the relationship above $[f(i) = c \; G_i \; (x, y, z)]$ are cartesian coordinates whereas xy from equation (13) are reduced variables:

$$f_i = c \; G_i \; (x, y)$$

for i=0 n
  c=cmax*i/n
  for j=0 m
    y=ymax*j/m
    x=func(c,y)
    for k=0 1
      f=cG$_k$(x,y)
      stamp$_{ij}$=stamp$_{ij}$+fftamp (@f)

stamp$_{ij}$ is the i,jth two-dimensional amplitude where i corresponds to the speed of sound c and j corresponds to the length of resonance factor y.

fftamp (@f) is the FFT power spectrum amplitude at frequency f.

EXAMPLE

The results shown in FIGS. 1-5 were acquired from the flare line at the Phillips Petroleum pilot plant in Bartlesville, Okla. At the time of the test, only the roots of the first seven 1 values of the first three principle quantum numbers (N=1, 2, 3) had been calculated, or a total of 21 were used to develop the basis set for the AT. An example of one of the two-dimensional roots is shown in FIG. 1.

Figure 2A:
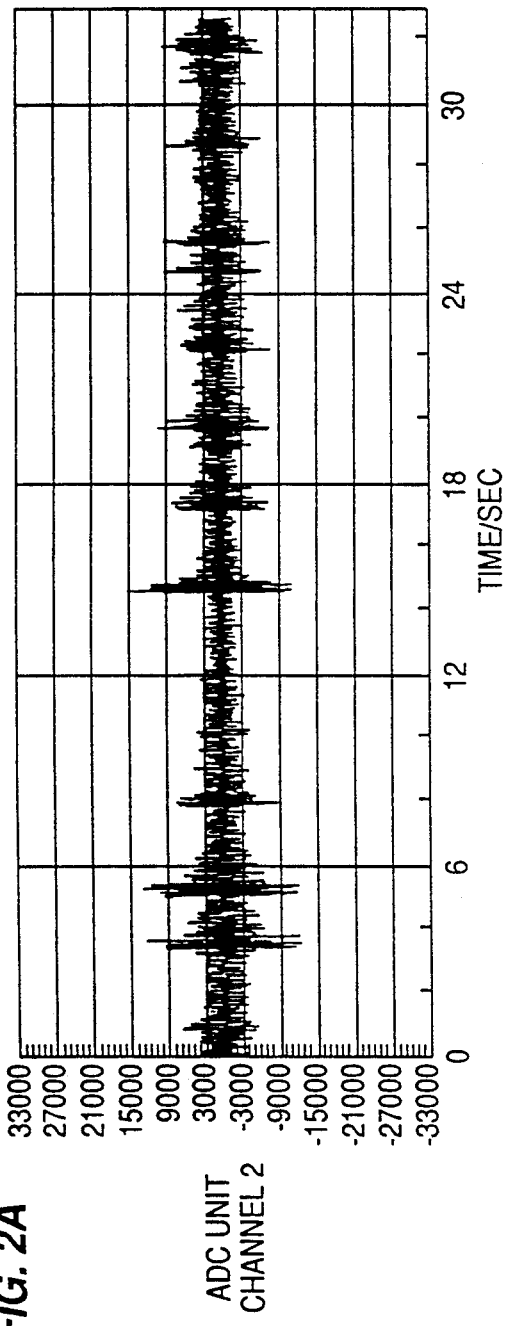
Figure 2B:
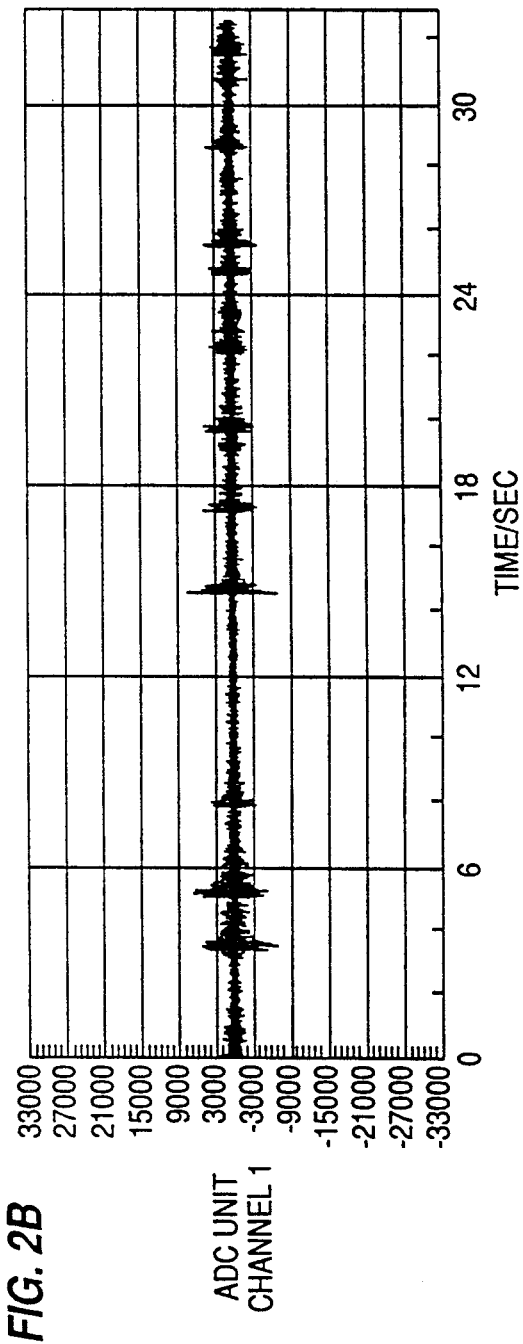

A plot of two signals, acquired simultaneously at two points one meter apart, are shown in FIG. 2.

Figure 3A:
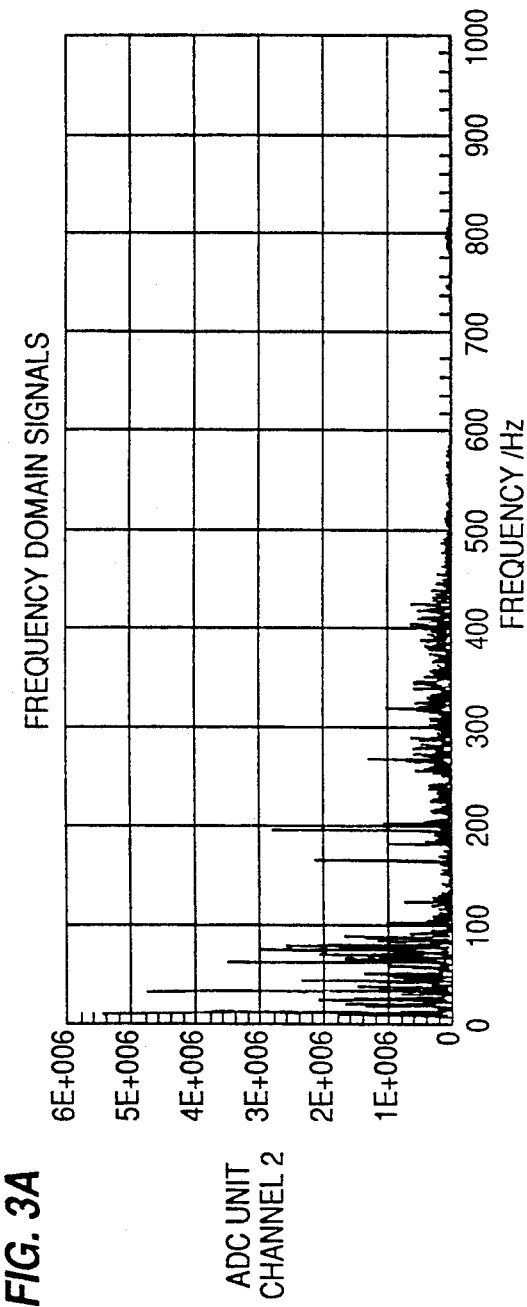
Figure 3B:
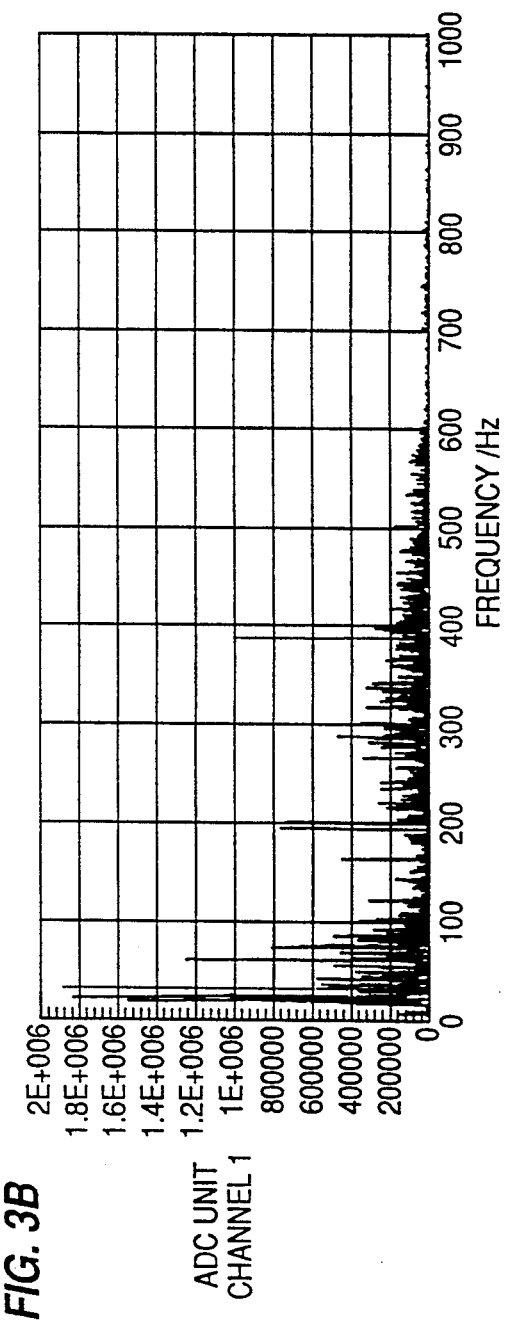

Two signals were transformed into the frequency domain via an FFT as shown in FIG. 3.

Figure 4:
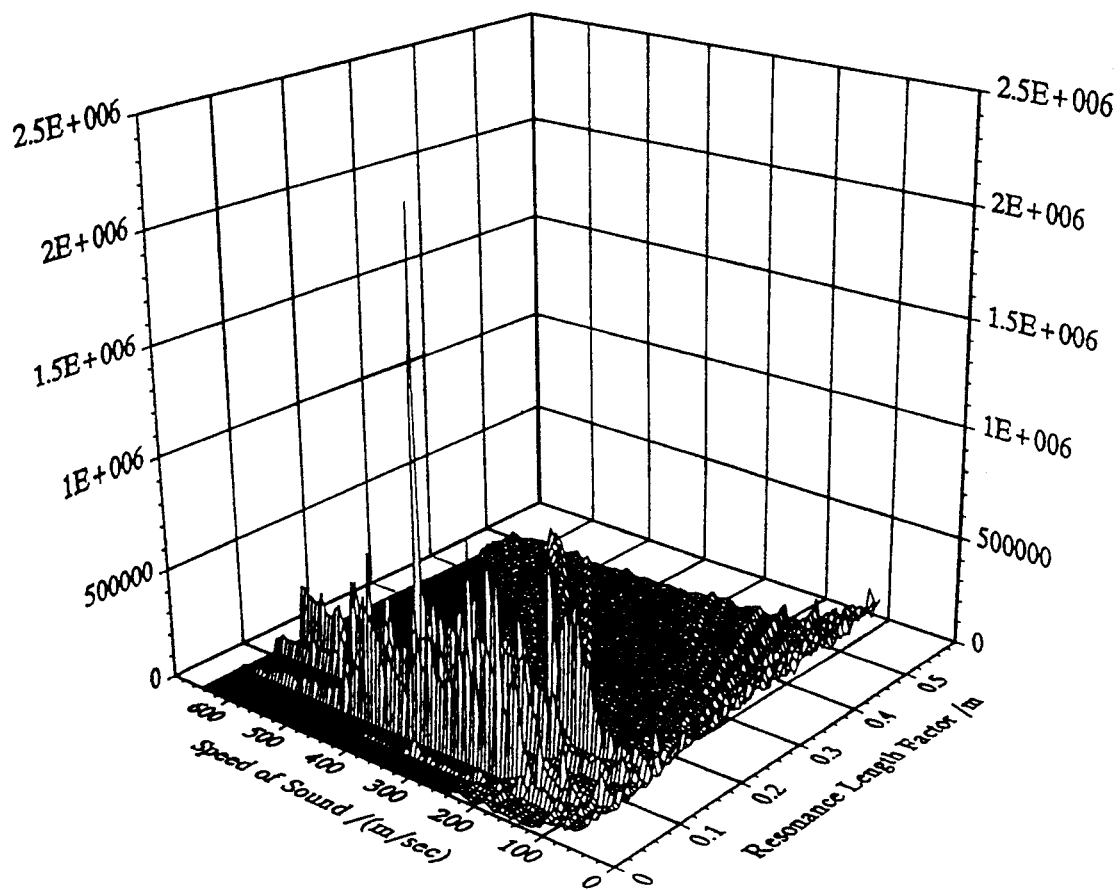

A single frequency domain is then transformed into the two-dimensional sonic domain as shown in FIG. 4. The length of resonance factor is simply the intermediate term z shown in equation (12). The highest weighted speed of sound is easily determined by sorting of amplitudes (or by inspection) to be 443.5 m/sec, which is precisely the speed of sound of the mixture of methane and nitrogen that was flowing through the pipe.

A number of acquisitions were stored on disk over a period of approximately one hour. A series of transformations were performed individually and the highest weighted speed of sound was recorded to disk. A resulting acoustigraph is shown in FIG. 5.

The acoustigraph shows a baseline at approximately 443.5 m/sec which is the flow through the flare when nothing is being dumped. As different hoods and reactors dump their heavy contents to the flare, the speed of sound drops accordingly. Some hoods contain hydrogen which causes the speed of sound to increase. In any case, the results of the acoustigraph match the weekly compositional analysis reports of the flare line.

Several volume flow measurement techniques already exist on the market (e.g., ultrasonic doppler flow meter, magnetic flow meter), but none of these are passive and all require calibration. The benefit of acquiring the speed of sound is that the speed of sound is a state variable and this technique produces an absolute measurement of this state variable. This is analogous to the development of a thermometer which also measures another state variable passively. In a three-dimensional world, if one knows three state variables, one can calculate all state variables (e.g., entropy, enthalpy and heat capacity). This can be easily facilitated by measuring temperature, pressure or volume flow along with the speed of sound. Perhaps the easiest of the three would be simply the temperature and the volume flow. If one knows the composition of the gas in the pipe, then even mass flow can be calculated. Or if one has a sample of the gas, a numerical equation of state can be measured and stored in a database that can be used to produce an extremely accurate density, of course, once the density is known along with the volume flow, then the mass flow is also known along with all other extensive state variables.

The only limitation of this device's resolution is the speed and size of the processing computer. No in-the-field changes need be made as the computer technology improves; simply a change in the algorithm is required.

We claim:

1. A passive, non-invasive method of measuring the flow and composition of a fluid or mixture of fluids through a structure within a system by:
   attaching a thermometer, a pressure gauge, and a transducer to said structure for respectively detecting temperature, pressure, and sound in said fluid or mixture of fluids;
   producing sounds corresponding to naturally occurring vibrations stimulated by flow of said fluid or mixture of fluids through said structure;
   passing said sounds through said fluid or mixture of fluids;
   detecting said sounds exiting from said fluid or mixture of fluids by use of said transducer;
   determining the temperature, pressure and speed of sound in said fluid or mixture of fluids in said system by respectively using said thermometer, said pressure gauge and said fluid or mixture of fluids and calculating the flow, molar density and average molecular weight of the fluid from the equation:

$$c^2 = \frac{\tau}{M} \left( \frac{\delta P}{\delta \rho} \right)_T;$$

$$\nabla^2 \phi = \frac{1}{c^2} \frac{\delta^2 \phi}{\delta t^2}$$

$$\tau = \frac{c_P}{c_\rho}$$

wherein:
$c_P$ = isobaric heat capacity
$C_\rho$ = isochoric heat capacity
$c$ = speed of sound
$P$ = pressure of the fluid
$T$ = temperature of the fluid
$\rho$ = molecular density of the fluid
$M$ = average molecular weight of the fluid
$\phi$ = velocity potential
$t$ = time;

(a) the molar density of the fluid being determined from the equation of state over a small temperature range $T-T'$:

$$\left( \frac{\delta P}{\delta \rho} \right)_T = f(P, c)_{T'}.$$

wherein:
f = any EOS
$T'$ = average temperature; and (b) the average molecular weight of the fluid being determined from the equation:

$$\frac{c^2}{f(P, c)_T} = \frac{\tau}{M}$$

wherein: f = EOS;
said temperature, pressure and speed of sound being determined, respectively, by means of a thermometer, pressure gauge and transducer positioned in said system.

2. The method of claim 1 wherein said system is a pipe.

3. The method of claim 1 wherein said system is a turbine.

4. The method of claim 1 wherein said system is a chimney.

* * * * *